United States Patent
van Hal

(10) Patent No.: US 11,029,248 B2
(45) Date of Patent: Jun. 8, 2021

(54) DETERMINING A CONTAMINATION LEVEL OF A FLUID SAMPLE

(71) Applicant: Schlumberger Technology Corporation, Sugar Land, TX (US)

(72) Inventor: Ronald E. G. van Hal, Belmont, MA (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 645 days.

(21) Appl. No.: 15/621,145

(22) Filed: Jun. 13, 2017

(65) Prior Publication Data

US 2017/0363542 A1 Dec. 21, 2017

Related U.S. Application Data

(60) Provisional application No. 62/352,095, filed on Jun. 20, 2016.

(51) Int. Cl.
| | |
|---|---|
| G01N 21/3577 | (2014.01) |
| G01N 33/28 | (2006.01) |
| G01N 21/359 | (2014.01) |
| E21B 49/10 | (2006.01) |

(52) U.S. Cl.
CPC ......... G01N 21/3577 (2013.01); E21B 49/10 (2013.01); G01N 21/359 (2013.01); G01N 33/28 (2013.01)

(58) Field of Classification Search
CPC .. G01N 21/3577; G01N 21/359; G01N 33/28; E21B 49/10

USPC ............................................................ 702/13
See application file for complete search history.

(56) References Cited

U.S. PATENT DOCUMENTS

| | | | | |
|---|---|---|---|---|
| 4,253,766 | A * | 3/1981 | Funk | G01N 21/314 |
| | | | | 356/418 |
| 6,274,865 | B1 | 8/2001 | Schroer et al. | |
| 6,350,986 | B1 | 2/2002 | Mullins et al. | |
| 8,024,125 | B2 | 9/2011 | Hsu et al. | |
| 2008/0156088 | A1* | 7/2008 | Hsu | E21B 49/10 |
| | | | | 73/152.23 |
| 2016/0178599 | A1* | 6/2016 | Gisolf | E21B 49/087 |
| | | | | 73/23.35 |

OTHER PUBLICATIONS

Kentaro Indo et al., "Estimation of Fluid Composition From Downhole Optical Spectrometry," Presented at the SPE Annual Technical Conference and Exhibition held in New Orleans, Louisiana, USA, Sep. 30-Oct. 2, 2013 SPE 166464, (21 pages).

* cited by examiner

*Primary Examiner* — Toan M Le
*Assistant Examiner* — Xiuqin Sun
(74) *Attorney, Agent, or Firm* — Eileen Pape

(57) ABSTRACT

In some examples, an optical density of a contaminant in a fluid sample is computed. An optical density of a target fluid in the fluid sample is computed using optical densities of the fluid sample at a plurality of wavelengths. Based on the computed optical density of the contaminant and the computed optical density of the target fluid, a level of contamination by the contaminant in the fluid sample is determined.

11 Claims, 6 Drawing Sheets

DETERMINING A CONTAMINATION LEVEL OF A FLUID SAMPLE

RELATED APPLICATIONS

The present document is based on and claims priority to U.S. Provisional Application Ser. No. 62/352,095, filed Jun. 20, 2016, entitled "Determining a Contamination Level of a Fluid Sample" to Ronald van Hal, which is incorporated herein by reference in its entirety.

BACKGROUND

The following descriptions and examples are not admitted to be prior art by virtue of their inclusion in this section.

Drilling, completion, and production of wells involve measuring various subsurface formation parameters. A well operator can measure amounts of different types of fluids (such as oil, water, gas, and so forth) contained in a sample of a fluid mixture drawn from wells to determine formation fluid quality. Based on the measured amounts of the different fluid types in the fluid mixture, it can be determined whether it is economical to extract a target fluid (e.g., a hydrocarbon) from a reservoir surrounding a well. Obtaining accurate measurements of a fluid sample relies on the fluid sample being substantially free of contaminants.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In accordance with one embodiment, a method of a system is provided comprising a processor. The method comprises receiving optical densities of a fluid sample at a plurality of wavelengths, the fluid sample comprising a target fluid and a contaminant and computing an optical density of the contaminant. In addition, the method further comprises computing an optical density of the target fluid using the received optical densities of the fluid sample at the plurality of wavelengths and determining, based on the computed optical density of the contaminant and the computed optical density of the target fluid, a level of contamination by the contaminant in the fluid sample.

In accordance with another embodiment, a method of a system comprising a processor is provided. The method includes receiving optical densities of a fluid sample at a plurality of wavelengths, the fluid sample comprising a target fluid and a contaminant and computing optical densities of the contaminant at the plurality of wavelengths. In addition the method includes computing optical densities of the target fluid at the plurality of wavelengths based on the received optical densities of the fluid sample at the plurality of wavelengths using a relationship between optical densities at multiple wavelengths for a first type of formation fluid and computing a composition of the target fluid based on the computed optical densities of the target fluid.

Still further, the method includes determining, based on the composition, whether the target fluid is of a second type of formation fluid different from the first type of formation fluid and in response to determining that the target fluid is of a second type of formation fluid different from the first type of formation fluid, re-computing optical densities of the target fluid at the plurality of wavelengths based on the received optical densities of the fluid sample at the plurality of wavelengths using a relationship between optical densities at multiple wavelengths for the second type of formation fluid. Additionally, the method includes determining, based on the computed optical densities of the contaminant and the re-computed optical densities of the target fluid, a level of contamination by the contaminant in the fluid sample.

In accordance with still another embodiment, a non-transitory storage medium is provided that stores instructions that upon execution cause a system to receive optical densities of a fluid sample at a plurality of wavelengths, the fluid sample comprising a target fluid and a contaminant and determine a correlation factor based on a relationship between target fluid optical densities at the plurality of wavelengths. In addition, upon execution the system is caused to compute an optical density of the target fluid using the correlation factor and determine, based on the computed optical density of the target fluid, a level of contamination by the contaminant in the fluid sample.

In accordance with yet another embodiment, a system is provided including at least one processor to receive optical densities of a fluid sample at a plurality of wavelengths, the fluid sample comprising a formation fluid and a contaminant, and compute an optical density of the formation fluid using the received optical densities of the fluid sample at the plurality of wavelengths. In addition, the processor determines, based on the computed optical density of the formation fluid, a level of contamination by the contaminant in the fluid sample.

Other or alternative features will become apparent from the following description, from the drawings, and from the claims.

BRIEF DESCRIPTION OF THE DRAWINGS

Certain embodiments will hereafter be described with reference to the accompanying drawings, wherein like reference numerals denote like elements. It should be understood, however, that the accompanying drawings illustrate only the various implementations described herein and are not meant to limit the scope of various technologies described herein. The drawings are as follows.

DETAILED DESCRIPTION

Figure 1:
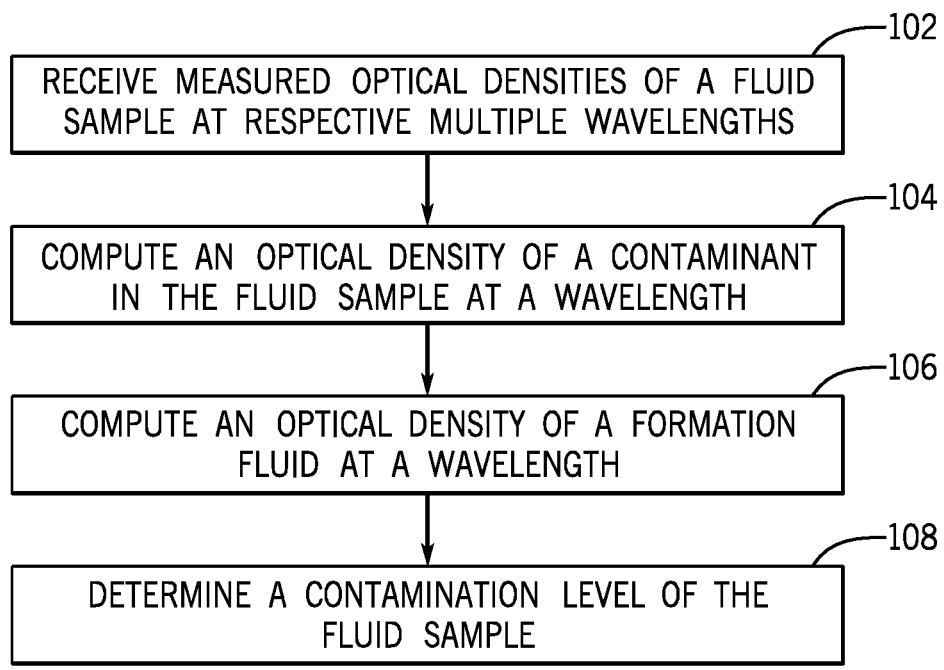
FIG. 1 is a flow diagram of an example process to determine a contamination level of a fluid sample, according to some implementations.

Reference throughout the specification to "one embodiment," "an embodiment," "some embodiments," "one aspect," "an aspect," or "some aspects" means that a particular feature, structure, method, or characteristic described in connection with the embodiment or aspect is included in at least one embodiment of the present disclosure. Thus, the appearance of the phrases "in one embodiment" or "in an embodiment" or "in some embodiments" in various places throughout the specification are not necessarily all referring to the same embodiment. Furthermore, the particular features, structures, methods, or characteristics may be combined in any suitable manner in one or more embodiments. The words "including" and "having" shall have the same meaning as the word "comprising."

When a well is being drilled, a drilling mud (more generally referred to as a drilling fluid) is introduced into the well as a lubricant to reduce the effects of friction between a drill bit of a drill string and a wall of the well. The drilling mud can also be used to keep the drill bit cool during use, as well as to maintain a hydrostatic pressure in the well. A drilling mud (or equivalently a drilling fluid) includes a liquid or a mixture of different liquids. In some cases, a drilling mud (or drilling fluid) can also contain a solid.

Contamination of formation fluid occurs when a mud filtrate of the drilling mud permeates into the formation surrounding the well during and after drilling. A mud filtrate of the drilling mud refers to the liquid component of the drilling mud. A formation fluid can refer to a fluid that is stored in a reservoir contained in the formation. Examples of formation fluids include hydrocarbons such as oil, gas, and/or other fluids.

After or during a well drilling process, formation fluid samples can be collected and analyzed to determine a formation fluid quality based on measuring relative amounts of different materials in the formation fluid samples. Due to the use of a drilling mud, formation fluid samples often contain a mixture of formation fluid and mud filtrate. The amount of mud filtrate in a formation fluid sample indicates the contamination level (i.e., the amount of contamination) of the formation fluid sample. If the mud filtrate is miscible with the formation fluid (e.g., such as when an oil-based drilling mud is used), the mud filtrate contamination in the formation fluid can reduce the quality of formation fluid samples and make subsequent analysis unreliable.

A collected fluid sample can be analyzed in a well, at a well site, or in a laboratory. As examples, the analysis of the fluid sample can be used to determine compositions of different fluids in a fluid mixture, such as fractions of methane, ethane, propane, pentane, and so forth, in the fluid mixture.

To obtain more accurate results in the analysis of a fluid sample, it is desired that the contamination level in the fluid sample be below a specified threshold. However, accurate determination of the contamination level of a fluid sample can be challenging. As formation fluids are pumped from the formation, the amount of contaminants in the formation fluids is reduced over time. However, the amount of time involved to obtain clean fluid samples (i.e., fluid samples where the contamination level is below a specified threshold) can last from an hour to more than 24 hours, so that a well operator is unable to determine when fluid samples are clean enough to perform accurate analysis of collected fluid samples. Using techniques according to some implementations of the present disclosure, contamination levels of fluid samples can be determined so that clean fluid samples can be identified and collected on which analysis can be performed.

Additionally, techniques according to some implementations of the present disclosure can also be used to predict a composition of a fluid sample, even if the fluid sample is contaminated with a contaminant.

In the ensuing discussion, reference is made to analyzing a formation fluid sample collected in a well. More generally, techniques or mechanisms according to some implementations can be applied to analyze other types of fluid samples, including fluid samples collected from other sources outside a well environment. Such other types of fluid samples can include a target fluid (i.e., the fluid of interest), and possibly a contaminant.

In accordance with some implementations of the present disclosure, techniques or mechanisms are provided to monitor contamination levels in fluid samples collected in a well. In the present discussion, although reference is made to the contaminant in a fluid sample as being a mud filtrate, it is noted that in other examples, other types of contaminants can be included in a fluid sample collected in a well that is to be analyzed. In some examples, real-time monitoring of contamination levels in fluid samples can be performed in a well. For example, a tool (such as a drilling tool or other type of tool) in the well can include one or more sensors that are able to make measurements of fluid samples. In other examples, monitoring of contamination levels in fluid samples can be performed by a wireline tool, such as a formation tester that is run into a well on a wireline (which includes a cable that has electrical or other type of communication media). In yet further examples, monitoring of contamination levels in fluid samples can be performed by other types of downhole tools. As measurements are being made of the fluid samples, the analysis can be performed as such measurements are made. Such analysis is referred to as real-time analysis. The analysis on the measurements acquired by the sensor(s) can be performed by a computer at the earth surface above the well, or in other examples, can be performed by a computer that is part of the downhole tool that is in the well.

In further examples, instead of performing a real-time analysis of measurements acquired of the fluid sample by sensor(s), the analysis can be performed offline at a later time after the measurements have been made.

In some implementations of the present disclosure, determining the contamination level can include a two-part process. A first part involves the determination of an optical density (also referred to as an optical absorbance) of the contaminant, which in some examples includes a mud filtrate. An optical density of a material can represent a power attenuation of incident light on the material caused by absorption and/or refraction of light by the material. A second part of the process includes determining the optical density of a target formation fluid (e.g., a formation oil) that is to be drawn from the formation surrounding the well. For a mixture of formation fluid and mud filtrate, a measured optical density at a particular wavelength (λ) is linearly related to a contamination level. As the contamination level in a fluid sample changes, the measured optical density of the fluid sample changes to indicate the changing contamination level.

The optical density of a fluid sample at a certain wavelength follows the Beer Lambert law. The Beer Lambert law defines a linear relationship between optical absorbance (i.e., optical density) and concentrations of materials in measured fluid samples. Accordingly, the Beer Lambert law can be used as a basis to determine the buildup of formation oil concentrations relative to contaminants in fluid samples. For a fluid sample containing a mixture of formation oil and mud filtrate, the measured optical density (OD) of the fluid sample at a wavelength (λ) (i.e., $OD_\lambda$) is linearly related to the contamination level (η) in the fluid sample according to Eq. 1 below.

$$OD_\lambda = \eta OD_{\lambda,fil} + (1-\eta) OD_{\lambda,oil}. \quad \text{(Eq. 1)}$$

The contamination level, η, can range in value between 0 and 1, with 0 indication no contamination, while a value greater of η greater than zero represents a percentage of the fluid sample that is made up of contaminants. In other examples, the contamination level can be represented using other amounts. To determine the contamination level (η) based on Eq. 1, the optical density ($OD_{\lambda,fil}$) of the contaminant, e.g., the mud filtrate, and the optical density $OD_{\lambda,oil}$ of the formation fluid, e.g., formation oil, have to be known. However, these values are not known a priori and thus have to be determined based on use of the two-part process according to some implementations of the present disclosure.

FIG. 1 shows an example two-part process for determining a contamination level of a fluid sample according to some implementations. The process of FIG. 1 can be performed by a computer, such as a computer at the earth surface or by a computer in a downhole tool that is deployed in a well.

The process of FIG. 1 receives (at 102) measured optical densities of the fluid sample at respective multiple wavelengths. For example, the optical densities of the fluid sample can be measured by one or more sensors of a downhole tool. The fluid sample includes a formation fluid (such as formation oil) and a contaminant (such as mud filtrate). In some implementations, the measured optical densities can include at least two measurements measured at two different timestamps, to enable to determination of computing an optical density of a contaminant and an optical density of a formation fluid as discussed further below.

The process then determines (at 104) an optical density of a contaminant (e.g., mud filtrate), in the fluid sample, at a respective wavelength. In some examples, optical densities of the contaminant can be determined at respective multiple wavelengths. The multiple wavelengths can range from visible wavelength light to mid-infrared wavelength light, including near-infrared light. Different wavelengths can have different sensitivities to the contaminant. Although different wavelengths have different sensitivities to the contaminant, the optical density measured at a given wavelength nonetheless contains some valuable information about the contamination level in the fluid sample.

The process of FIG. 1 then determines (at 106) an optical density of a formation fluid (e.g., a formation oil) at a respective wavelength. In some examples, optical densities of the formation fluid can be determined at respective multiple wavelengths. The determination of the optical density of the formation fluid uses a technique according to some implementations of the present disclosure that is based on optical density measurements of the fluid sample at two or more wavelengths, and a relationship between formation fluid optical densities at multiple wavelengths derived from a database or prior computation. The database can be populated using past measurements in the same well or in similar wells. More generally, the database can include measurements from wells across the world, from wells in a given region, from wells at a specific locality, or from different zones of the same well. The database includes correlated formation fluid optical densities at respective wavelengths. Using this database, the relationship between optical densities of a fluid sample at different wavelengths can be derived.

The process of FIG. 1 then determines (at 108) a contamination level (represented as η in Eq. 1) of the fluid sample using the measured optical densities of the fluid sample received at 102, and the determined optical densities derived at 104 and 106. Multiple contamination levels can be computed for respective wavelengths of multiple wavelengths using Eq. 1, i.e., $OD_\lambda = \eta OD_{\lambda,fil} + (1-\eta) OD_{\lambda,oil}$.

In further examples, there are use cases where measured optical densities (as received at 102) are made at just one timestamp, as opposed to multiple timestamps. Such examples are possible where the spectrum of optical densities of the mud filtrate at multiple wavelengths is already known or has been previously derived. For example, this can be possible when the analysis is performed with respect to multiple zones of one well. A prior analysis may have computed the spectrum of optical densities of the mud filtrate for a first zone. The previously computed spectrum for the mud filtrate can be used for the analysis of a second zone in the same well.

More generally, the process of FIG. 1 can be used to determine the contamination level of a fluid sample that includes a target fluid and a contaminant. The target fluid is a fluid of interest, which in the case of well production can include a formation fluid. However, in other contexts, the target fluid can be a different type of fluid from a different source.

Determining an Optical Density of a Contaminant

The following describes an example technique for determining the optical density of a contaminant at a respective wavelength in task 104 discussed above. The following assumes that the contaminant is mud filtrate. However, similar techniques can be used to determine the optical density of other contaminants in other examples.

In some examples, mud filtrate does not contain methane and is colorless, whereas a formation fluid such as formation oil can contain methane and has a color. These differences between the mud filtrate and the formation oil can be used to determine the optical density of the mud filtrate as discussed below.

Under normal circumstances, the amount of contamination in fluid samples can be reduced during pumping (to extract formation fluid from the formation reservoir). However, some short-term fluctuations in contamination levels can occur during pumping. Measurements at different times (such as at two different times t1 and t2) generally will follow the general trend line of declining levels of contamination as pumping continues. The measured optical densities of fluid samples at multiple time points (t1 and t2) can be used to calculate the differential optical density at a wavelength λ.

$$OD_{\lambda,dif} = OD_{\lambda,t1} - OD_{\lambda,t2}, \quad \text{(Eq. 2)}$$

where $OD_{\lambda,dif}$ is the differential optical density at wavelength λ, and $OD_{\lambda,t1}$ and $OD_{\lambda,t2}$ are the optical densities of fluid samples at times t1 and t2, respectively, at wavelength λ. The differential optical density is based on the difference between the optical density of a fluid sample ($OD_{\lambda,t1}$) at time t1, and the optical density of a fluid sample ($OD_{\lambda,t2}$) at time t2.

The fact that mud filtrate has almost no optical density at visible wavelengths or the fact that mud filtrate does not contain methane can be used to determine a correlation factor (c) (also referred to as a correlation factor) that represents a relationship between the optical densities of the fluid samples at the different time points that can be used to compute the optical density of the mud filtrate. For example, at the wavelength of 680 nanometers (nm), an optical density of a synthetic, diesel or distillation cut based mud filtrate is −0.028 (for a 2 millimeter (mm) path length and a quartz cuvette). This value is dependent on the specific material of the mud filtrate and can vary for different materials. In the foregoing example that assumes a wavelength of 680 nm, the multiplication factor then becomes:

$$c = \frac{OD_{680,t1} + p}{OD_{680,dif}}, \quad \text{(Eq. 3)}$$

where p is equal to 0.028 in the example above, but can be a different value for other materials or other wavelengths.

Once the multiplication factor c is derived, the optical density of the mud filtrate can be calculated by:

$$OD_{\lambda,fil} = OD_{\lambda,t1} - c \cdot OD_{\lambda,dif} \quad \text{(Eq. 4)}$$

According to Eq. 4, the optical density of the mud filtrate ($OD_{\lambda,fil}$) is derived from the optical density of the fluid sample ($OD_{\lambda,t1}$) at time t1, less the product of the multiplication factor (c) and the differential optical density ($OD_{\lambda,dif}$). Eq. 4 can be used to calculate optical densities of the mud filtrate at multiple wavelengths $\lambda$.

In some examples, the optical densities of the mud filtrate across the multiple wavelengths can be checked for any irregularities. For example, the visible wavelengths should not show a sharp decline at the shortest wavelength and should be more or less linear as function of wavelength.

Determining an Optical Density of a Formation Fluid

The same differential optical density ($OD_{\lambda,dif}$) discussed above can be used to determine the optical density of the formation fluid at task 106 in FIG. 1. However, there are no wavelengths at which the formation oil does not absorb light and mud filtrate does absorb light. Therefore, a different technique (from the technique discussed above for computing the optical density of the mud filtrate) is used to compute a correlation factor (d) (also referred to as a multiplication factor) that can be used to compute the optical density of the formation fluid, such as formation oil. The multiplication factor (d) is based on the relationship between optical densities of a fluid sample at multiple wavelengths.

In some examples, the relationship between optical densities of a fluid sample at multiple wavelengths that can be exploited to determine the multiplication factor (d) is based on the fact that the curve shapes of methylene ($CH_2$) vibrations are quite similar for formation oils, and these $CH_2$ vibrations are distinct from those of the base oils used in drilling muds. This distinction originates from the fact that base oils contain just a small subset of the components in formation oils.

The following describes several different techniques for computing the optical density of the formation fluid using respective differently calculated multiplication factors (d).

Technique 1

Figure 2:
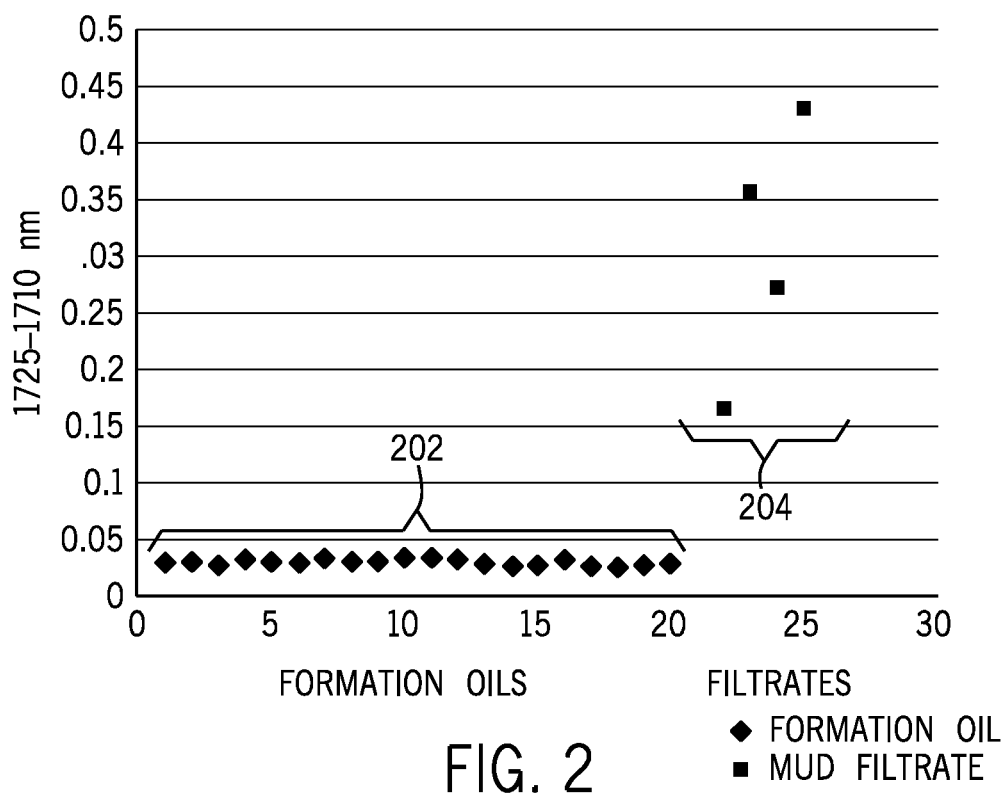
FIGS. 2-5 are example plots illustrating various relationships that can be used to determine an optical density of a formation fluid, according to some implementations.

In a first technique, a multiplication factor (d) is computed based on a difference between the optical density of a formation fluid (e.g., formation oil) at a first wavelength and an optical density of the formation fluid (e.g., formation oil) at a second wavelength. In an example according to FIG. 2, the first wavelength is 1710 nm and the second wavelength is 1725 nm. As shown in FIG. 2, the difference in optical densities of different formation oils is approximately constant, which in the example of FIG. 2 is approximately 0.03. Although a specific example value is depicted in FIG. 2, it is noted that in other examples, the difference between optical densities of a formation oil at different wavelengths can have another value. More generally, for a given formation oil, the approximately constant difference between the optical density of the given formation oil at the first wavelength and the optical density of the given formation oil at the second wavelength is represented as k.

FIG. 2 is a plot of differences between optical densities at respective wavelengths (which in the example of FIG. 2 are differences between optical densities at the 1725 nm and 1710 nm wavelengths) with respect to different oils, including different formation oils and different mud filtrates. Examples of different formation oils include those from different formations, and examples of different mud filtrates include those including different base oil groups, such as diesel, mineral oil, paraffin, and so forth.

In FIG. 2, a diamond-shaped point 202 represents the optical density difference between optical densities of a formation oil at the 1725 nm wavelength and the 1710 nm wavelength. Different diamond-shaped points 202 represent different optical density differences for different formation oils. In FIG. 2, a square-shaped point 204 represents the optical density difference between optical densities of a mud filtrate at the 1725 nm wavelength and the 1710 nm wavelength. Different square-shaped points 204 represent different optical density differences for different mud filtrates.

The points of FIG. 2 can be based on past measurements and analyses that have been collected in a database, from different wells.

Assuming the example where the first wavelength is 1710 nm and the second wavelength is 1725 nm, the multiplication factor (d) can be computed according to:

$$d = \frac{OD_{1725,t2} - OD_{1710,t2} - k}{OD_{1725,dif} - OD_{1710,dif}}. \quad \text{(Eq. 5a)}$$

In Eq. 5a, $OD_{1725,t2}$ represents the optical density of a fluid sample at the 1725 nm wavelength collected at time t2, $OD_{1710,t2}$ represents the optical density of a fluid sample at the 1710 nm wavelength collected at time t2, $OD_{1725,dif}$ represents the difference between optical densities of a fluid sample at the 1725 nm wavelength collected at respective times t1 and t2, and $OD_{1710,dif}$ represents the difference in optical densities of a fluid sample at the 1710 nm wavelength collected at respective times t1 and t2.

In other examples, other wavelengths can be used as the first and second wavelengths to compute the multiplication factor (d). More generally, Eq. 5a can be expressed as:

$$d = \frac{OD_{\lambda 2,t2} - OD_{\lambda 1,t2} - k}{OD_{\lambda 2,dif} - OD_{\lambda 1,dif}}, \quad \text{(Eq. 5b)}$$

where $\lambda 1$ is the first wavelength, and $\lambda 2$ is the second wavelength.

Once d is derived, the optical density of the formation oil ($OD_{\lambda,oil}$) can be calculated by:

$$OD_{\lambda,oil} = OD_{\lambda,t2} - d \cdot OD_{\lambda,dif} \quad \text{(Eq. 6)}$$

where $OD_{\lambda,t2}$ is the measured optical density of a fluid sample (containing a mixture of a formation oil and a mud filtrate) at time t2, and $OD_{\lambda,dif}$ is the difference in optical densities of the fluid sample at times t1 and t2.

Once the optical densities of the formation oil at respective wavelengths are derived, as computed according to Eq. 6, and the optical densities of the mud filtrate at respective wavelengths are derived, as computed according to Eq. 4, then the relationship expressed by Eq. 1 can be used to determine a contaminant level in the respective fluid sample.

Technique 2

A second technique of computing the multiplication factor and the optical density of the formation oil is described below. With this second technique, the multiplication factor (d) is derived based on a linear relationship between optical densities of formation fluids (e.g., formation oils) at a first wavelength (e.g., 1710 nm) and optical densities at a second wavelength (e.g., 1725 nm). An example of such a linear relationship is expressed by a curve 302 in FIG. 3, which is a plot where the horizontal axis corresponds to optical densities at the second wavelength (e.g., 1725 nm), and the vertical axis corresponds to optical densities at the first wavelength (e.g., 1710 nm).

Figure 3:
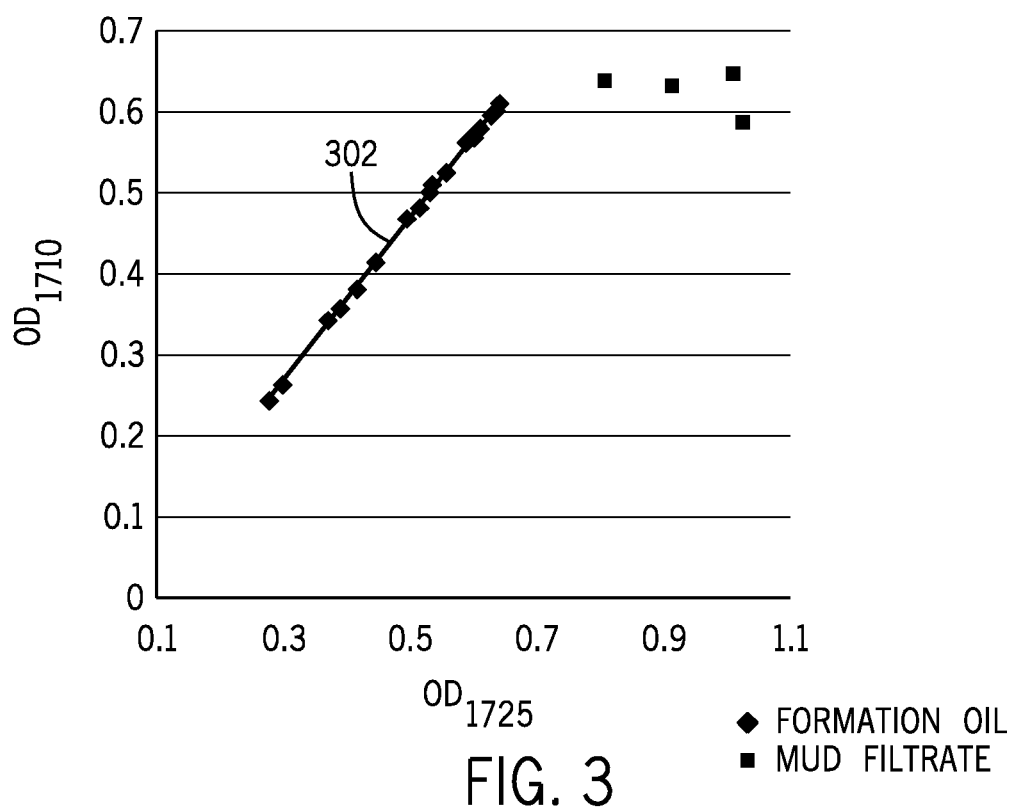

In FIG. 3, a point along the vertical axis represents an optical density of a formation oil (diamond-shaped point) or a mud filtrate (square-shaped point) at 1710 nm, and a point along the horizontal axis represents an optical density of a formation oil (diamond-shaped point) or a mud filtrate (square-shaped point) at 1725 nm.

The curve 302 is a line that is fit onto the diamond-shaped points (which represent different formation oils) on the plot shown in FIG. 3. A diamond-shaped point in the plot of FIG. 3 represents a respective formation fluid, and this point has a respective optical density at 1710 nm and a respective optical density at 1725 nm.

The points of FIG. 3 can be based on past measurements and analyses that have been collected in a database, from different wells.

The curve 302 has the following relationship y=ax−b, where y represents the vertical axis, x represents the horizontal axis, a represents the slope of the curve 302, and b is the offset along the vertical direction. The relationship between the optical densities of formation oils at 1710 nm and the optical densities of formation oils at 1725 nm is thus given by:

$$OD_{1710}=OD_{1725}*a-b. \quad \text{(Eq. 7)}$$

This linear relationship expressed by Eq. 7 can then be used to determine the multiplication factor (d) using:

$$d = \frac{(OD_{1710,t2} - OD_{1725,t2}*a + b)}{(OD_{1725,dif}*a - OD_{1710,dif})}. \quad \text{(Eq. 8a)}$$

Eq. 8a can be rewritten in a more general fashion by replacing 1710 nm and 1725 nm with λ1 and λ2, respectively, as follows:

$$d = \frac{(OD_{\lambda1,t2} - OD_{\lambda2,t2}*a + b)}{(OD_{\lambda2,dif}*a - OD_{\lambda1,dif})}. \quad \text{(Eq. 8b)}$$

The optical density of the formation oil can then be calculated by:

$$OD_{\lambda,oil}=OD_{\lambda,t2}-d*OD_{\lambda,dif}. \quad \text{(Eq. 9)}$$

Once the optical densities of the formation oil at respective wavelengths are derived, as computed according to Eq. 9, and the optical densities of the mud filtrate at respective wavelengths are derived, as computed according to Eq. 4, then the relationship expressed by Eq. 1 can be used to determine a contaminant level in the respective fluid sample.

Technique 3

Figure 4:
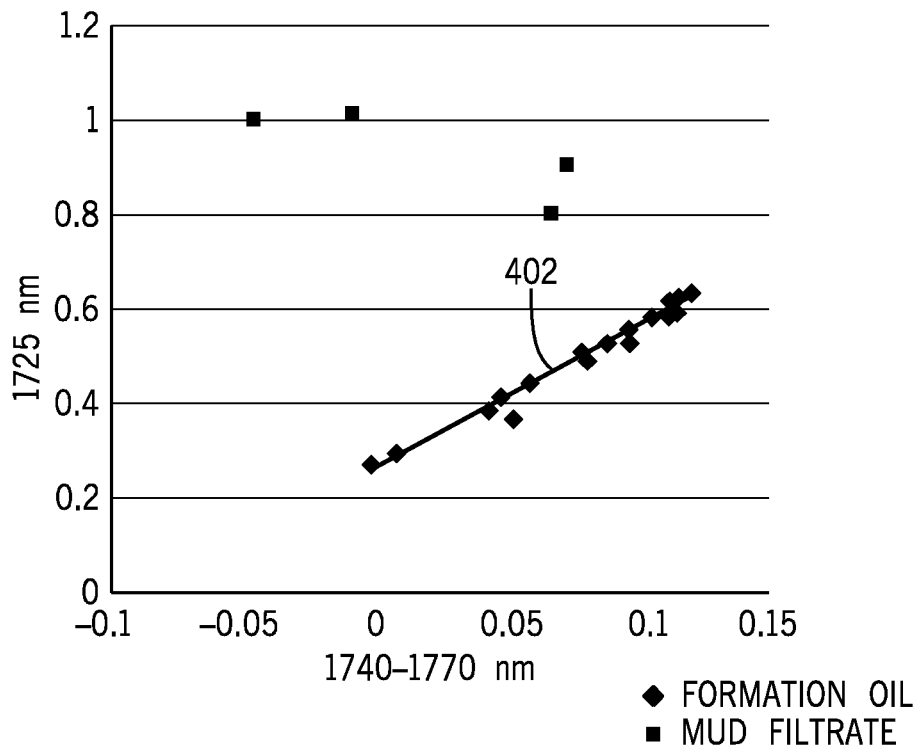

With a third technique, to compute the multiplication factor (d), the relationship between optical densities of a fluid sample at multiple wavelengths can be expressed as a ratio between an optical density at a first wavelength and a difference between optical densities at two wavelengths. FIG. 4 is a plot of the relation between optical densities at 1725 nm (the vertical axis) and differences between optical densities at 1740 nm and 1770 nm (the horizontal axis). A point on the vertical axis represents the optical density of a formation oil (diamond-shaped point) or mud filtrate (square-shaped point) at 1725 nm, while a point on the horizontal axis represents the difference between optical densities at 1740 nm and 1770 nm.

This relationship is represented by the curve 402, which is a line that is fit onto the diamond-shaped points. The curve 402 has the following linear relationship y=fx+g. The relationship between optical densities at 1725 nm and the differences between optical densities at 1740 nm and 1770 nm can thus be expressed as:

$$OD_{1725}=f*(OD_{1740}-OD_{1770})+g. \quad \text{(Eq. 10)}$$

This relationship can then be used to determine the multiplication factor (d) using:

$$d = \frac{(OD_{1725,t2} - (OD_{1740,t2} + OD_{1770,t2})*f - g)}{(f*(OD_{1740,dif} - OD_{1770,dif}) - OD_{1725,dif})}. \quad \text{(Eq. 11a)}$$

Eq. 11a can be rewritten in a more general fashion by replacing 1725 nm, 1740 nm, and 1770 nm with λ1, λ2, and λ3, respectively, as follows:

$$d = \frac{(OD_{\lambda1,t2} - (OD_{\lambda2,t2} + OD_{\lambda3,t2})*f - g)}{(f*(OD_{\lambda2,dif} - OD_{\lambda3,dif}) - OD_{\lambda1,dif})}. \quad \text{(Eq. 11b)}$$

The optical density of the formation oil can then be calculated by:

$$OD_{\lambda,oil}=OD_{\lambda,t2}-d*OD_{\lambda,dif}. \quad \text{(Eq. 12)}$$

Once the optical densities of the formation oil at respective wavelengths are derived, as computed according to Eq. 12, and the optical densities of the mud filtrate at respective wavelengths are derived, as computed according to Eq. 4, then the relationship expressed by Eq. 1 can be used to determine a contaminant level in the respective fluid sample.

Technique 4

A fourth technique expresses the relationship of optical densities at multiple wavelengths based on the relationship between differences in optical densities of a first set (e.g., first pair) of wavelengths and differences between optical densities of a second set (e.g., second pair) of wavelengths, where the second set of wavelengths is different from the first set of wavelengths. A first set of wavelengths that is different from a second set of wavelengths can refer to first and second sets where at least one of the wavelengths in one set is not present in the other set.

Figure 5:
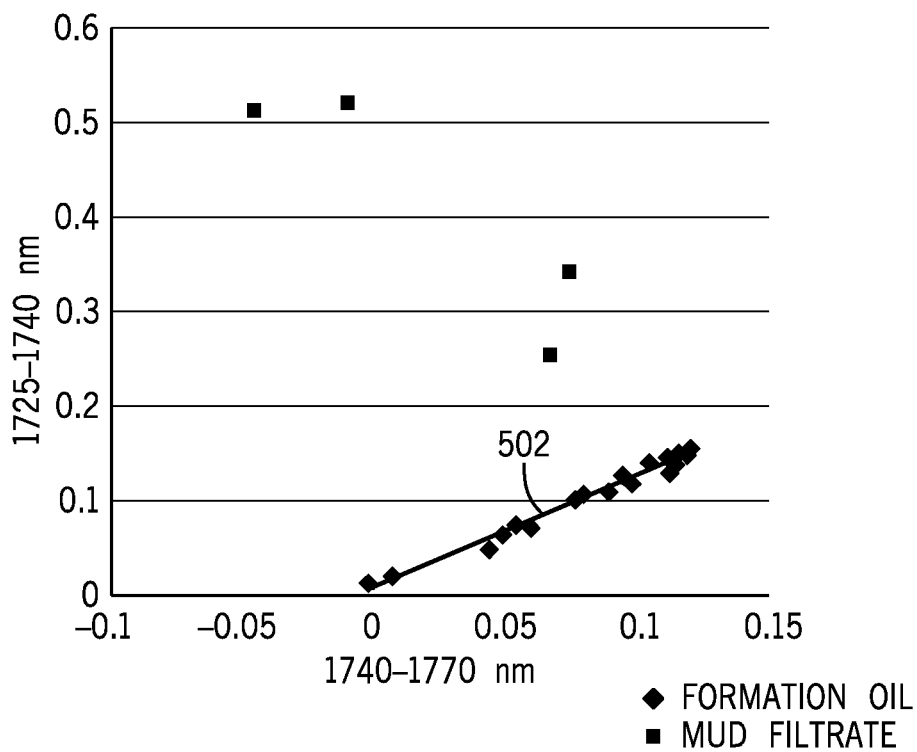

FIG. 5 shows a relationship between differences in optical densities of a first set of wavelengths (difference of optical densities at 1725 nm and 1740 nm), as represented by the vertical axis, and differences in optical densities of wavelengths of a second set of wavelengths (including 1740 nm and 1770 nm). A curve 502 is fitted through diamond-shaped points in FIG. 5 that represent respective different formation oils. The curve 502 has the following linear relationship y=hλ+i.

Thus, $$OD_{1725}-OD_{1740}=(OD_{1740}-OD_{1770})*h+i. \quad \text{(Eq. 13)}$$

This relation can be used to determine the multiplication factor (d):

$$d = \frac{((OD_{1740,t2} - OD_{1770,t2}) * h - OD_{1725,t2} + OD_{1740,t2} - i)}{(OD_{1725,dif} - OD_{1740,dif} + h * (OD_{1770,dif} - OD_{1740,dif}))}. \quad \text{(Eq. 14a)}$$

Eq. 14 can be rewritten in a more general fashion by replacing 1725 nm, 1740 nm, and 1770 nm with λ1, λ2, and λ3, respectively, as follows:

$$d = \frac{((OD_{\lambda2,t2} - OD_{\lambda3,t2}) * h - OD_{\lambda1,t2} + OD_{\lambda2,t2} - i)}{(OD_{\lambda1,dif} - OD_{\lambda2,dif} + h * (OD_{\lambda3,dif} - OD_{\lambda2,dif}))}. \quad \text{(Eq. 14b)}$$

The optical density of the formation oil can then be calculated by:

$$OD_{\lambda,oil} = OD_{\lambda,t2} - d * OD_{\lambda,dif} \quad \text{(Eq. 15)}$$

Once the optical densities of the formation oil at respective wavelengths are derived, as computed according to Eq. 15, and the optical densities of the mud filtrate at respective wavelengths are derived, as computed according to Eq. 4, then the relationship expressed by Eq. 1 can be used to determine a contaminant level in the respective fluid sample.

Although specific techniques are described above, it is noted that in other examples, other techniques can be employed for computing the optical density of a formation oil or other formation fluid.

By determining the contamination levels in fluid samples, an accurate contamination level of the fluid in a flow conduit (where formation fluid is extracted to the well surface), can be determined. In response to determining that the contamination level in the flow conduit has reached below a specified threshold, then a fluid sample can be collected for analysis.

As discussed above, various techniques (e.g., Techniques 1-4 or other techniques) can be used to compute the optical densities of a formation fluid at multiple wavelengths. The computed optical densities across the spectrum of wavelengths can also be used to determine the composition of the formation fluid according to techniques that use optics to determine a sample composition of the formation fluid. The composition of the formation fluid can be determined from a fluid sample that is contaminated, i.e., has a contamination level that is greater than a specified threshold.

Any one of several different composition prediction techniques can be used to compute the composition of a fluid sample based on optical absorbance (the optical densities discussed herein).

The optical densities of a formation fluid at various wavelengths computed using any of the optical density computation techniques discussed further above can form an optical density spectra (i.e., a collection of optical densities of a formation fluid at multiple wavelengths). A relationship can be established to predict the composition of a fluid sample based on the optical density spectra as follows:

$$y = xB, \quad \text{(Eq. 16)}$$

where x is a vector that represents the computed optical density spectra, B represents a mapping matrix (or other mapping relationship), which can be obtained based on a database containing composition information and optical density spectra, and y is a vector that represents relative amounts (e.g., relative mass concentrations) of the components of the fluid mixture in a fluid sample. The vector y thus quantifies the composition of the fluid sample. In some examples, the vector y can include the relative mass concentrations of the following components in the fluid sample: $C_1$ (methane), $C_2$ (ethane), $C_3$ (propane), $C_4$ (butane), $C_5$ (pentane), $C_{6+}$ (hexane or higher molecular weight components), and $CO_2$ (carbon dioxide). Further details regarding computation of a composition using Eq. 16 can be found in Kentaro Indo et al., "Estimation of Fluid Composition From Downhole Optical Spectrometry," Society of Petroleum Engineers, SPE 166464, December 2015.

In other examples, other techniques based on an algorithm developed from the Beer Lambert law can be used to determine a fluid composition of a fluid sample from optical densities of a formation fluid at multiple wavelengths. The Beer-Lambert's law indicates that the optical absorption of a component is proportional to its concentration.

Using techniques according to some implementations, the "endpoints" of a fluid sample at any given point in time can be computed. Such "endpoints" include a first endpoint where 100% contaminant is present (i.e., no formation fluid), which corresponds to the optical density of the contaminant computed as discussed above, and a second endpoint where 100% formation fluid is present (i.e., no contaminant), which corresponds to the optical density of the formation fluid computed as discussed above. Knowledge of the endpoints enables the calculation of a contamination level at any given point in time. This can be used to determine the endpoints of any measurement that has linear mixing laws. An example of such a measurement can be density.

Measurements that do not follow linear mixing laws can be monitored continuously and based on experience an endpoint can be determined. An example of measurements that do not follow linear mixing laws include measurements of viscosity. The viscosity of a fluid does not have a linear relation with respect to the ratio of the viscosity of two pure fluids. Measurements of viscosity can have a nonlinear relation that has a smooth curve without steps. As a result, if the contamination level of a fluid sample can be derived at any time, the curve can be reconstructed, assuming that there are a sufficient number of data points.

In the foregoing discussion, techniques for computing the optical densities of a formation fluid at respective wavelengths is based on a relationship between optical densities at multiple wavelengths for oil, such as illustrated as 202, 302, 402, and 502 in respective FIGS. 2-5. It is noted that the relationship between optical densities at multiple wavelengths can differ for a different type of formation fluid, such as gas condensate or gas. Gas condensate refers to a liquid form of gas.

Figure 6:
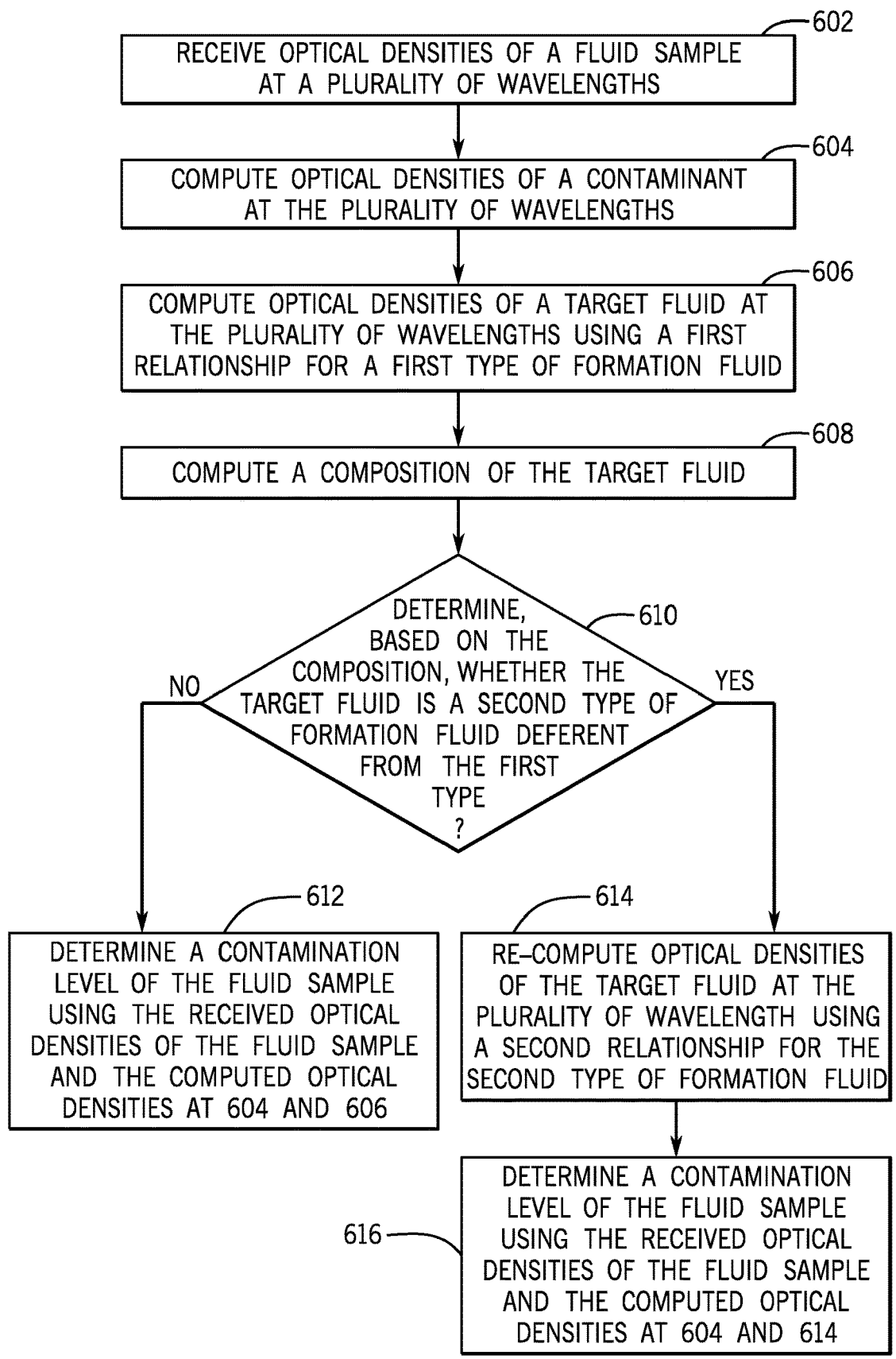
FIG. 6 is a flow diagram of another example process to determine a contamination level of a fluid sample, according to further implementations.

FIG. 6 is a flow diagram of an example process for determining a contaminant level in a fluid sample that takes into account differences in relationships between optical densities for different types of formation fluid: oil, gas condensate, and gas.

The process of FIG. 6 receives (at 602) optical densities of a fluid sample at a plurality of wavelengths, the fluid sample including a target fluid and a contaminant. The process computes (at 604) optical densities of the contaminant at the plurality of wavelengths. The process computes (at 606) optical densities of the target fluid at the plurality of wavelengths based on the received optical densities of the fluid sample at the plurality of wavelengths using a first relationship between optical densities at multiple wavelengths for a first type of formation fluid (e.g., oil).

The process computes (at 608) a composition of the target fluid based on the computed optical densities of the target fluid, such as by using Eq. 16 above. The process determines (at 610), based on the composition, whether the target fluid is of a second type of formation fluid different from the first type of formation fluid. If not, the process determines (at 612) a contamination of the fluid sample using the received optical densities of the fluid sample received at 602, and the computed optical densities derived at 604 and 606. Determining the type of the target fluid can be based on the relative amounts of the different components within the target fluid. For example, oil, gas condensate, and gas will have relatively different amounts of the following components: $C_1$, $C_2$, $C_3$, $C_4$, $C_5$, $C_{6+}$, and $CO_2$.

However, in response to determining that the target fluid is of a second type of formation fluid (e.g., gas condensate or gas) different from the first type of formation fluid, the process re-computes (at 614) optical densities of the target fluid at the plurality of wavelengths based on the received optical densities of the fluid sample at the plurality of wavelengths using a relationship between optical densities at multiple wavelengths for the second type of formation fluid. The process then determines (at 616), based on the computed optical densities of the contaminant (604) and the re-computed optical densities of the target fluid (614), a level of contamination by the contaminant in the fluid sample.

Environments

Figure 7:
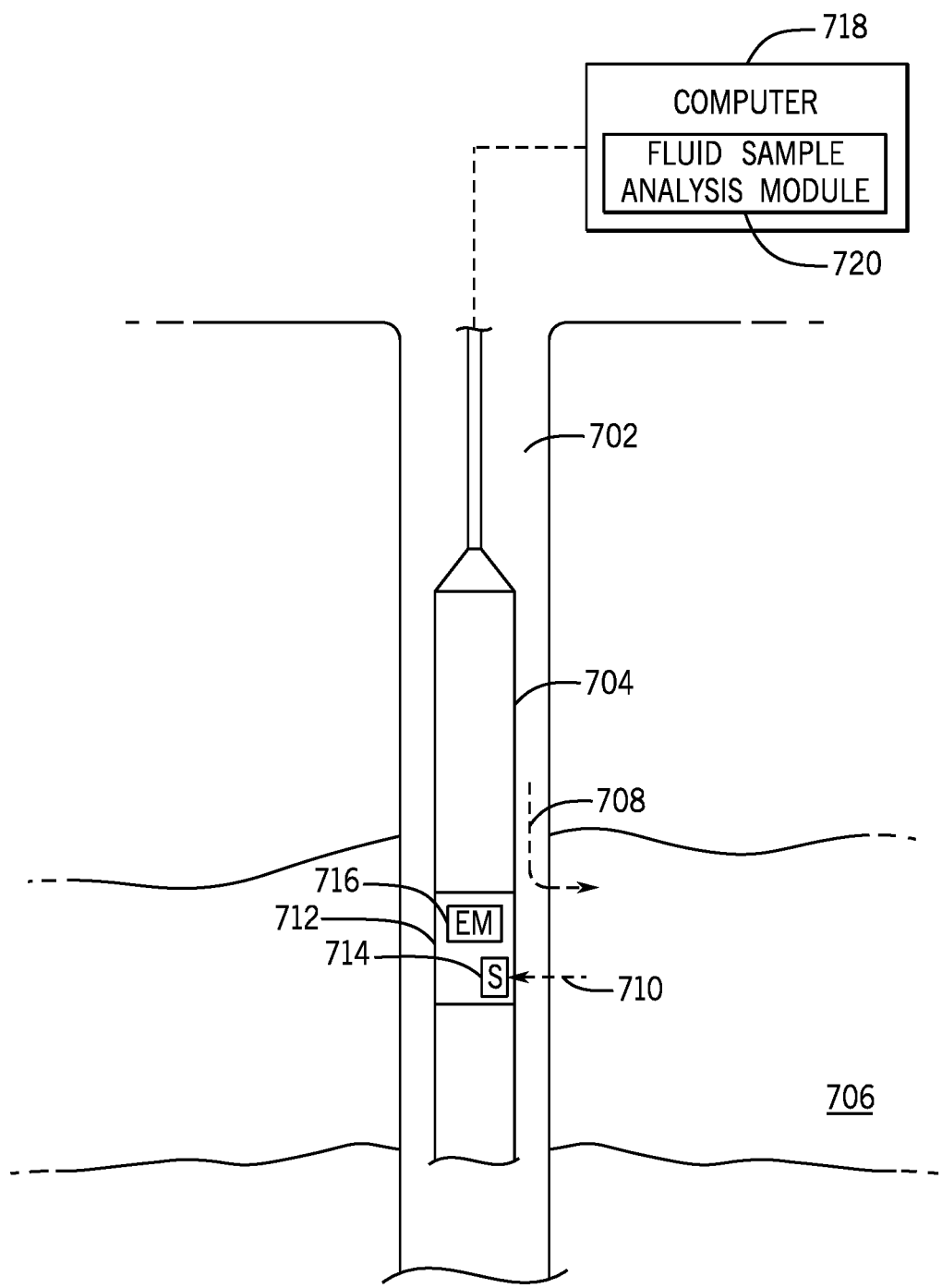
FIG. 7 is a block diagram of an example arrangement that includes a downhole tool having a formation tester, in accordance with some implementations.

FIG. 7 is a block diagram of an example arrangement that includes a well 702 and a downhole tool 704 deployed in the well 702. In some examples, the downhole tool 604 can include a drill string to drill the well 702. In other examples, the downhole tool 704 can be a different type of tool.

As discussed above, during drilling, a drilling mud is injected into the well 702. The drilling mud conveyed into the well 702 can be maintained at a pressure that can be higher than the pressure of fluid ("pore pressure") in the surrounding formation 706, to prevent formation fluid from passing from the surrounding formation 706 into the well 702.

Keeping the pressure of the drilling mud relatively higher than the pore pressure causes mud filtrate from the drilling mud to enter or permeate (indicated generally by arrow 708) a layer (up to some depth) into the surrounding formation 706. As a result, fluid samples subsequently extracted from the formation 706 can be contaminated with the mud filtrate.

When fluid is initially drawn from the formation 706, the fluid will include a mix of the mud filtrate and the formation fluid. Using measurements of fluid samples contaminated with the mud filtrate to determine a quality of the formation 706 can produce inaccurate results that are not indicative of the true characteristics of the pure formation fluid of the formation 706. However, because the mud filtrate penetrates a finite distance into the formation 706, after extraction of fluid from the formation 706 has occurred for some extended period of time, the extracted fluid will contain relatively less contaminant than samples obtained during an initial pumping phase.

Techniques as discussed above can be used to determine the contamination level of a fluid sample.

The downhole tool 704 includes a formation tester 712 that can include one or more probes (not shown). A probe can extract fluid samples from the formation 606, generally along a direction indicated by arrow 710. A sensor 714, which may be part of the probe or in another location in the formation tester 712, can perform measurements of the extracted fluid samples.

The sensor 714 can include a spectrometer to measure an optical density of a fluid sample. As an example, the spectrometer can include one or more optical sources to output photons having energies corresponding to different wavelengths and multiple optical detectors for determining the intensity of the light sources at the various wavelengths as well as the intensity of the light transmitted through the fluid samples at those wavelengths. In other examples, other types of sensors or additional sensors can be employed in addition to the spectrometer.

The formation tester 712, or another component of the downhole tool 712, can include an electronic module 716 that includes a communications subsystem to communicate data with surface equipment at the earth surface above the well 702. In some examples, the communication of data between the communications subsystem and the surface equipment can be accomplished using acoustic signals propagated through the drilling mud or other fluid in the well 702.

The data that can be communicated by the communications subsystem to the surface equipment can include measurement data, including optical density measurements, collected by the one or more sensors 714.

The surface equipment can include a computer 718, which can execute a fluid sample analysis module 720. In some examples, the fluid sample analysis module 720 can receive optical density measurements from the formation tester 712 to determine a contamination level within a fluid sample, and/or to predict a composition of the fluid sample, as discussed above.

In other examples, the analysis of fluid samples to determine contamination levels and/or to predict composition of fluid samples can be performed by a processor subsystem that can be part of the electronic module 716 or elsewhere in the downhole tool 704.

In implementations where the contamination levels are determined downhole by the processor subsystem in the downhole tool 704, the downhole processor subsystem can control a fluid control assembly, including a valve or an arrangement of valves, based on the determined contamination level. The fluid control assembly is activated to route a fluid sample to a fluid store (including one or more tanks, for example) in response to determining that the contamination level of the fluid sample is below a specified threshold.

When the contamination level of a fluid sample is not below the specified threshold, the processor subsystem can control the fluid control assembly to route the fluid sample out of the formation tester 712 into a well region.

Figure 8:
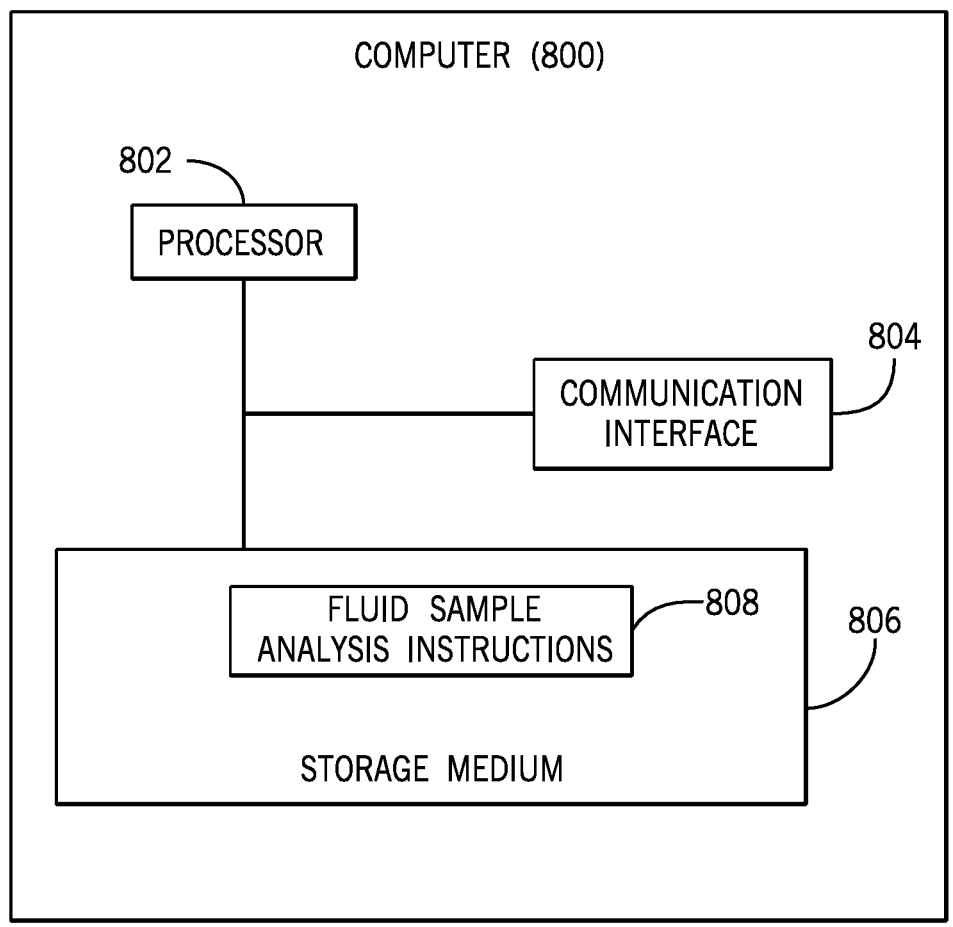
FIG. 8 is a block diagram of an example computer that incorporates some implementations in the present disclosure.

FIG. 8 is a block diagram of a computer 800 or other system, which can be the computer 718 that is part of the surface equipment of FIG. 7, or in other examples, can be the processor subsystem that is in the downhole tool 704 of FIG. 7. The computer 800 includes a processor (or multiple processors) 802, where a processor can include a microprocessor, a core of a multi-core microprocessor, a microcontroller, a programmable integrated circuit, a programmable gate array, or other processing hardware.

The processor(s) 802 can be coupled to a communication interface to communicate with a remote entity, and a non-transitory machine-readable or computer-readable storage medium 806 that can store fluid sample analysis instructions 808 that are executable on the processor(s) 802 to perform various tasks as discussed above. For example, the fluid sample analysis instructions 808 can be part of the fluid sample analysis module 720 of FIG. 7, or can execute in a downhole processor subsystem.

The storage medium 806 can include one or multiple different forms of memory including semiconductor memory devices such as dynamic or static random access memories (DRAMs or SRAMs), erasable and programmable read-only memories (EPROMs), electrically erasable and programmable read-only memories (EEPROMs) and flash memories; magnetic disks such as fixed, floppy and removable disks; other magnetic media including tape; optical media such as compact disks (CDs) or digital video disks (DVDs); or other types of storage devices. Note that the instructions discussed above can be provided on one computer-readable or machine-readable storage medium, or alternatively, can be provided on multiple computer-readable or machine-readable storage media distributed in a large system having possibly plural nodes. Such computer-readable or machine-readable storage medium or media is (are) considered to be part of an article (or article of manufacture). An article or article of manufacture can refer to any manufactured single component or multiple components. The storage medium or media can be located either in the machine running the machine-readable instructions, or located at a remote site from which machine-readable instructions can be downloaded over a network for execution.

In the foregoing description, numerous details are set forth to provide an understanding of the subject disclosed herein. However, implementations may be practiced without some of these details. Other implementations may include modifications and variations from the details discussed above. It is intended that the appended claims cover such modifications and variations.

What is claimed is:

1. A method of a system comprising a processor, comprising:
    receiving optical densities of a fluid sample at a plurality of wavelengths, the fluid sample comprising a target fluid and a contaminant;
    computing an optical density of the contaminant;
    determining a correlation factor based on a relationship between target fluid optical densities at multiple wavelengths;
    computing an optical density of the target fluid using the received optical densities of the fluid sample at the plurality of wavelengths and the correlation factor; and
    determining, based on the computed optical density of the contaminant and the computed optical density of the target fluid, a level of contamination by the contaminant in the fluid sample;
    wherein the relationship is between differences between optical densities of the target fluid at a first pair of wavelengths and differences between optical densities of the target fluid at a second pair of wavelengths where at least one of the wavelengths in one pair of the first and second pairs of wavelengths is not present in the other pair of the first and second pairs of wavelengths.

2. The method of claim 1, wherein the received optical densities comprise at least two optical densities of the fluid sample for at least two different timestamps.

3. The method of claim 1, wherein the target fluid is a formation fluid produced from a formation reservoir through a well, and wherein determining the level of contamination comprises determining the level of contamination by a mud filtrate in the fluid sample.

4. The method of claim 1, wherein the relationship is a constant value derived from a difference between optical densities of the target fluid at multiple wavelengths.

5. The method of claim 1, wherein the relationship comprises a linear relationship between optical densities of target fluids at multiple wavelengths.

6. The method of claim 1, wherein the computed optical density of the target fluid is at a first wavelength, the method further comprising:
    computing, using the correlation factor, optical densities of the target fluid at multiple wavelengths.

7. The method of claim 6, further comprising:
    predicting a composition of the fluid sample using the optical densities of the target fluid in a spectrum of wavelengths including the first wavelength and the multiple wavelengths.

8. The method of claim 1, further comprising:
    controlling a fluid control assembly in response to the determined level of contamination, wherein the controlling comprises:
        activating the fluid control assembly to route the fluid sample to a fluid store in response to the determined level of contamination being below a specified threshold.

9. A system comprising:
    at least one processor to:
        receive optical densities of a fluid sample at a plurality of wavelengths, the fluid sample comprising a formation fluid and a contaminant;
        determine a correlation factor based on a relationship between formation fluid optical densities at the plurality of wavelengths;
        compute an optical density of the formation fluid using the received optical densities of the fluid sample at the plurality of wavelengths and the correlation factor; and
        determine, based on the computed optical density of the formation fluid, a level of contamination by the contaminant in the fluid sample;
    wherein the relationship is between differences between optical densities of the target fluid at a first pair of wavelengths and differences between optical densities of the target fluid at a second pair of wavelengths where at least one of the wavelengths in one pair of the first and second pairs of wavelengths is not present in the other pair of the first and second pairs of wavelengths.

10. The system of claim 9, wherein the relationship is a constant value derived from a difference between optical densities of the formation fluid at multiple wavelengths.

11. The system of claim 9, wherein the relationship comprises a linear relationship between optical densities of formation fluids at multiple wavelengths.

* * * * *